(12) United States Patent
Jean

(10) Patent No.: US 9,220,448 B2
(45) Date of Patent: Dec. 29, 2015

(54) ULTRA-WIDE BAND NON-INVASIVE BIOLOGICAL SENSOR AND METHOD

(75) Inventor: Buford Randall Jean, Lorena, TX (US)

(73) Assignee: Baylor University, Waco, TX (US)

(*) Notice: Subject to any disclaimer, the term of this patent is extended or adjusted under 35 U.S.C. 154(b) by 625 days.

(21) Appl. No.: 13/577,852

(22) PCT Filed: Feb. 10, 2011

(86) PCT No.: PCT/US2011/024283
§ 371 (c)(1),
(2), (4) Date: Aug. 8, 2012

(87) PCT Pub. No.: WO2011/100390
PCT Pub. Date: Aug. 18, 2011

(65) Prior Publication Data
US 2012/0310055 A1 Dec. 6, 2012

Related U.S. Application Data

(60) Provisional application No. 61/303,171, filed on Feb. 10, 2010.

(51) Int. Cl.
*A61B 5/1455* (2006.01)
*A61B 5/145* (2006.01)
(Continued)

(52) U.S. Cl.
CPC ........... *A61B 5/14532* (2013.01); *A61B 5/0507* (2013.01); *A61B 5/4869* (2013.01); *A61B 5/7257* (2013.01)

(58) Field of Classification Search
CPC ... A61B 5/1455; A61B 5/14532; G01N 22/00
USPC ......... 600/309, 310, 322, 316, 331, 365, 368; 324/639, 642
See application file for complete search history.

(56) References Cited

U.S. PATENT DOCUMENTS 6,287,776 B1 * 9/2001 Hefti ........................... 435/6.11
6,987,393 B2    1/2006 Jean
(Continued)

FOREIGN PATENT DOCUMENTS

GB    2428093    1/2007

OTHER PUBLICATIONS

Green, "Design of a Microwave Sensor for Non-Invasive Determination of Blood-Glucose Concentration". MS Thesis, Baylor University (2005).*

(Continued)

*Primary Examiner* — Eric Winakur
*Assistant Examiner* — Chu Chuan (J J) Liu
(74) *Attorney, Agent, or Firm* — Locke Lord LLP

(57) ABSTRACT

The disclosure provides an electromagnetic (EM) sensor system and method that permits rapid and non-invasive measurement of blood glucose or other biological characteristics that exhibits a unique spectral signature, such as its complex electrical permittivity within the frequency range from near DC to microwave frequencies. Low-level EM signals are coupled through the skin and modified by electrical properties of the sub dermal tissues. These tissues essentially integrate with the sensor circuit as they interact with the transmitted EM energy. The guided-wave signal can be sampled and converted to a digital representation. The digital information can be processed and analyzed to determine the frequency-sensitive permittivity of the tissues and a determination of blood glucose level is made based upon the sensor output. The sensor design and method has wide-ranging applicability to a number of important measurement problems in industry, biology, medicine, and chemistry, among others.

24 Claims, 9 Drawing Sheets

(51) Int. Cl.
*A61B 5/05* (2006.01)
*A61B 5/00* (2006.01)

(56) References Cited

U.S. PATENT DOCUMENTS

| | | | |
|---|---|---|---|
| 7,221,169 B2* | 5/2007 | Jean et al. | 324/639 |
| 2004/0065158 A1 | 4/2004 | Schrepfer et al. | |
| 2010/0328164 A1* | 12/2010 | Huynh | 343/702 |

OTHER PUBLICATIONS

International Search Report for International Patent Application No. PCT/US2011/0024283; European Patent Office, dated May 3, 2011.

Written Opinion of the International Search Report for International Patent Application No. PCT/US2011/0024283; European Patent Office, dated May 3, 2011.

* cited by examiner

ULTRA-WIDE BAND NON-INVASIVE BIOLOGICAL SENSOR AND METHOD

CROSS REFERENCE TO RELATED APPLICATIONS

This application is an international application claiming the benefit of U.S. Provisional Application No. 61/303,171, entitled "Ultra-Wide Band Non-Invasive Biological Sensor and Method," filed Feb. 10, 2010.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

1. Field of the Invention

The disclosure relates generally to a system and method for non-invasive analysis of material compositions using electromagnetic energy. More specifically, the disclosure relates to a system and method for non-invasive analysis of biological material and fluids therein.

2. Description of the Related Art

According to the National Diabetes Information Clearinghouse, in 2007, diabetes cost the United States $174 billion. Indirect costs, including disability payments, time lost from work, and reduced productivity, totalled $58 billion. Direct medical costs for diabetes care, including hospitalizations, medical care, and treatment supplies, amounted to $116 billion. Diabetes has no known cure, but may be managed with diet, exercise, and medication.

The ability for diabetics to self-monitor blood glucose has been a key advancement for control of the disease. There remains considerable research into "minimally invasive" and "non-invasive" methods for measuring blood sugar. Minimally invasive monitors require smaller blood samples than traditional invasive methods. These monitors measure blood taken from the finger or forearm. Samples from the forearm where nerves are not as close together as on the finger may be more comfortable for patients. The user pierces the skin, obtains a sufficient amount of blood, which is then placed on a test strip attached to a monitor that reports the glucose. Despite the advancements in minimal invasive sensors, there is a need for a truly non-invasive device that avoids the piercing of the skin for measuring glucose in a patient.

U.S. Pat. No. 5,077,476, Rosenthal, describes a near infrared (NIR) sensor which claims non-invasive measurement of glucose. The operation of the sensor involves introducing NIR energy into a body part and measuring a reflected signal via a receiving device in close proximity to the point of signal application. The received signal is analyzed to estimate blood glucose levels. NIR sensors have been studied for many years and a satisfactory non-invasive sensor has not been produced for the general market. The NIR signal has characteristic response that is sensitive to many tissue parameters and isolating a glucose specific response has been problematic.

The FDA has approved a glucose monitoring system for continuous use over twelve hours that is quasi non-invasive in the sense that penetration of the skin with a needle or lancet is not required. Instead, an electrical current draws glucose-containing fluid through the skin via reverse iontophoresis. This fluid is then analyzed for its glucose content. The device is not the non-invasive monitor diabetics seek. It lags behind traditional invasive methods by approximately 18 minutes, causes skin irritation in up to 50% of its users, and requires daily calibration by invasive glucose monitoring. The method is not a replacement for the traditional measurement; rather it is used only as a supplemental method between normal testing. Patents explaining this technology are shown, for example, in U.S. Pat. Nos. 6,144,869, 6,141,573, and 7,052,472.

Other needs for non-invasive fluid analysis in a patient, such as cholesterol, hormone levels, and the like, also involve invasive procedures. In a similar manner as the above issues with glucose, these levels can also benefit from non-invasive devices and methods.

It is well known that electromagnetic ("EM") properties of most real world materials, including the complex electrical permittivity and the magnetic permeability, are frequency dependent. Permittivity is used to describe how an electric field affects and is affected by a dielectric medium. Permittivity is determined by the ability of a material to polarize in response to an externally applied field and thereby reduce the total electric field inside the material. Permittivity is often expressed as a relative permittivity $\in_r$ to the permittivity $\in_0$ of a vacuum. Thus, permittivity relates to a material's ability to transmit (or "permit") an electric field. The response of real world materials to external fields normally depends on the frequency of the field, because the material's polarization does not respond instantaneously to an applied field. Permittivity for materials can be expressed as a complex function to allow specification of magnitude and phase of the permittivity as a function of the angular frequency ($\omega$) of the applied field with real and imaginary components as follows:

$$\in_r(\omega)=\in_r'(\omega)-j\in_r''(\omega)$$

Magnetic permeability, as another form of a material's response to applied EM energy, can be compared with electrical permittivity in that it is the degree of magnetization of material from reordered magnetic dipoles in the material when responding to a magnetic field applied to the material. Magnetic permeability is often expressed as a relative permeability to permeability in a vacuum. Magnetic permeability is frequency dependent for real world materials and can include real and imaginary components.

Thus, information concerning the composition of the substance can be obtained by exposing the substance to EM energy at different frequencies and analyzing the response at each frequency. Typically, the method for measuring the frequency-dependent characteristics of materials involves sequentially generating each frequency of interest or continuously varying over a range of frequencies that includes the frequency of interest, exposing the substance to energy generated at each frequency (also known as a "sweeping" or a swept frequency analysis), measuring at each frequency a property of the material, such as electrical permittivity or magnetic permeability, of the substance to the energy to which it is exposed, and then analyzing some aspect of the response of the material to determine the desired parameter value at each of those frequencies. Currently available industrial sensors and composition analyzers are used to obtain information concerning the composition of a substance to be processed by analyzing the response of the substance to electromagnetic energy.

U.S. Pat. No. 5,331,284, Jean, et. al., describes a meter and method marketed as a guided microwave spectrometer (GMS) system that uses a different approach for obtaining frequency dependent information. In the GMS system, a broad-band measurement is performed by stepping sequentially through a range of frequencies ("sweeping") and measuring the transmission cutoff characteristics of a waveguide that contains the material under test. By analyzing this spectral response of the waveguide, the effects of the frequency-dependent electrical properties can be calibrated to yield multi-component analysis of various mixtures.

U.S. Pat. No. 6,987,393, Jean et al., describes use of ultra-wide band (UWB) pulse technology for the measurement of the frequency response of industrial measurement cells and pipes containing an unknown material whose electrical properties are to be measured. UWB pulse technology is used to provide a sequence of electromagnetic (EM) energy pulses of relatively short duration to generate a very broad frequency band of energy. These pulses are communicated to the substance to be analyzed. The response of the substance to the pulses is measured and analyzed to determine properties of the substance. Knowledge of the properties of the substance may then be usefully employed in an industrial or other process involving the substance. The substance interacting with the pulsed energy provided will produce dispersion of the pulses. This dispersion is a function of the characteristics of the substance and affects the shape, duration, phase, and time of arrival of the energy pulses coupled to a sampling pulse receiver. A response signal arising from interaction of the substance with the pulse of energy can be transformed with a Fourier mathematical transform to produce a signal indicative of a response of the substance to energy at different frequencies within the range of frequencies in the spectrum of the pulsed signal.

Despite the progress in this field for non-invasive analysis, substantial needs remain. For example, it has been noted that a general characteristic frequency curve of biological materials exposed to EM energy forms a generally cascading downward curve having multiple regions, where the frequency is the X-axis and the complex permittivity is the Y-axis. One example of this research is seen in "Permittivity of Human Skin in the Millimeter Wave Band" C. M. Alabaster, IEE Electronics Letters, Vol. 39, No. 21, 16 Oct. 2003, pp. 1521-2. The curve is defined by the property(ies) of the material being measured. No known instrument can be used to field test such multiple regions for general public use that is economically and commercially viable. Thus, the asserted usefulness of the study's underlying technology does not provide the acclaimed benefits to those who need it the most.

There remains a need for an improved system and method for non-invasive analysis of biological materials and fluids therein.

BRIEF SUMMARY OF THE INVENTION

The disclosure provides an electromagnetic (EM) sensor system and method that permits rapid and non-invasive measurement of blood glucose or other biological characteristics that exhibits a unique spectral signature, such as its complex electrical permittivity within the frequency range from near DC to microwave frequencies. Low-level EM signals are coupled through the skin and modified by electrical properties of the sub dermal tissues. These tissues essentially integrate with the sensor circuit as they interact with the transmitted EM energy. The guided-wave signal can be sampled and converted to a digital representation. The digital information can be processed and analyzed to determine the frequency-sensitive permittivity of the tissues and a determination of blood glucose level is made based upon the sensor output. The sensor design and method has wide-ranging applicability to a number of important measurement problems in industry, biology, medicine, and chemistry, among others.

The disclosure provides a sensor and related method with one or more resonators tuned to respond at certain resonant frequencies that collectively reveal one or more characteristics of a material. The material can be biological material, such as blood, and one exemplary characteristic can be a glucose level in the blood.

More particularly, when EM energy in the form of a propagating EM signal is generated and the material is exposed to the signal, the material disperses the energy in the input signal, creating a distorted output signature. The signature can be mapped and calibrated for a given characteristic. The signature changes as the given characteristic changes. To identify the characteristic and its changes, a sensor with one or more frequency resonant elements creates an effective approximate short-circuit or impedance minimum at a desired resonant frequency. When the signal travels along a transmission line and a particular frequency passes through the resonant element and matches the resonant frequency, the resonant elements create an effective short-circuit and remove or reduce the signal at the frequency for which the short-circuit occurs from the propagating signal. The resonant element creates a null or dip in an output signal for that frequency. By choosing the proper frequency to effectively ground and create a null in the output signal, and then analyzing the resulting output, the output signal can indicate whether a characteristic is present, such as low or high glucose level in blood. More particularly, the placement of the null in the output, its magnitude, and/or shape can be used to indicate the presence of the characteristic. The sensor and method provide a readily available and cost effective solution to field sensing a characteristic of a material, particularly a characteristic that uses multiple regions in an EM energy versus frequency curve.

The disclosure provides a sensor system for measuring changes in electromagnetic energy in a biological material to be analyzed, comprising: a transmission line adapted to conduct an input signal of electromagnetic energy from a generator, the input signal composed of a series of ultra-wide-band (UWB) pulses; and a resonant circuit coupled to the transmission line and comprising one or more lumped or distributed element circuit components to define a resonant frequency for the resonant circuit, at least one of the one or more lumped or distributed element circuit components being adapted for coupling with the biological material to be analyzed such that a circuit value of the resonant circuit is responsive to the material to be analyzed, the resonant circuit adapted to cause the input signal on the transmission line to attenuate toward a null value as a frequency content of the input signal approaches the resonant frequency.

The disclosure further provides a sensor system for measuring changes in electromagnetic energy in a biological material to be analyzed, comprising: a generator adapted to generate an input signal of electromagnetic energy; a sensor coupled to the generator and adapted to receive the input signal from the generator; a receiver coupled to the sensor and adapted to receive a sensor output from the sensor; and a controller and processor coupled to the generator, the receiver, or a combination thereof and adapted to control a generation of the input signal from the generator, to process the sensor output from the receiver, or a combination thereof, the controller or processor configured to determine a biological characteristic of the biological material to be analyzed. The sensor can include a transmission line adapted to conduct the input signal of electromagnetic energy from the generator; and a resonant circuit coupled to the transmission line and comprising one or more lumped element or distributed element circuit components that define a resonant frequency for the resonant circuit, at least one of the one or more lumped element or distributed element circuit components being adapted for coupling with the biological material to be analyzed such that a circuit value of the resonant circuit is responsive to the material to be analyzed, the resonant circuit adapted to cause the input signal on the transmission line to attenuate toward a null value as a frequency content of the input signal approaches the resonant frequency.

The disclosure also provides a method of measuring one or more characteristics of a material responsive to electromagnetic energy, comprising: generating a signal of electromagnetic energy; providing the signal as input to a sensor disposed at least in proximity to the material to affect the input signal as the input signal is transmitted through the material; transmitting the signal along a transmission line of the sensor, the transmission line having one or more resonant circuits coupled to the transmission line, the resonant circuits having a resonant frequency particular to such resonant circuit and at least one of the resonant circuits having a resonant frequency that is affected by the material; creating a short-circuit condition in one or more of the resonant circuits when a frequency content of the electromagnetic energy approaches the resonant frequencies of the one or more resonant circuits; receiving an output signal from the sensor, the output signal representative of the input signal being subjected to a short-circuit condition during transmission through the sensor at frequencies approaching the resonant frequencies of the one or more resonant circuits; and processing the output signal to determine the one or more characteristics of the material.

DETAILED DESCRIPTION

Figure 1:
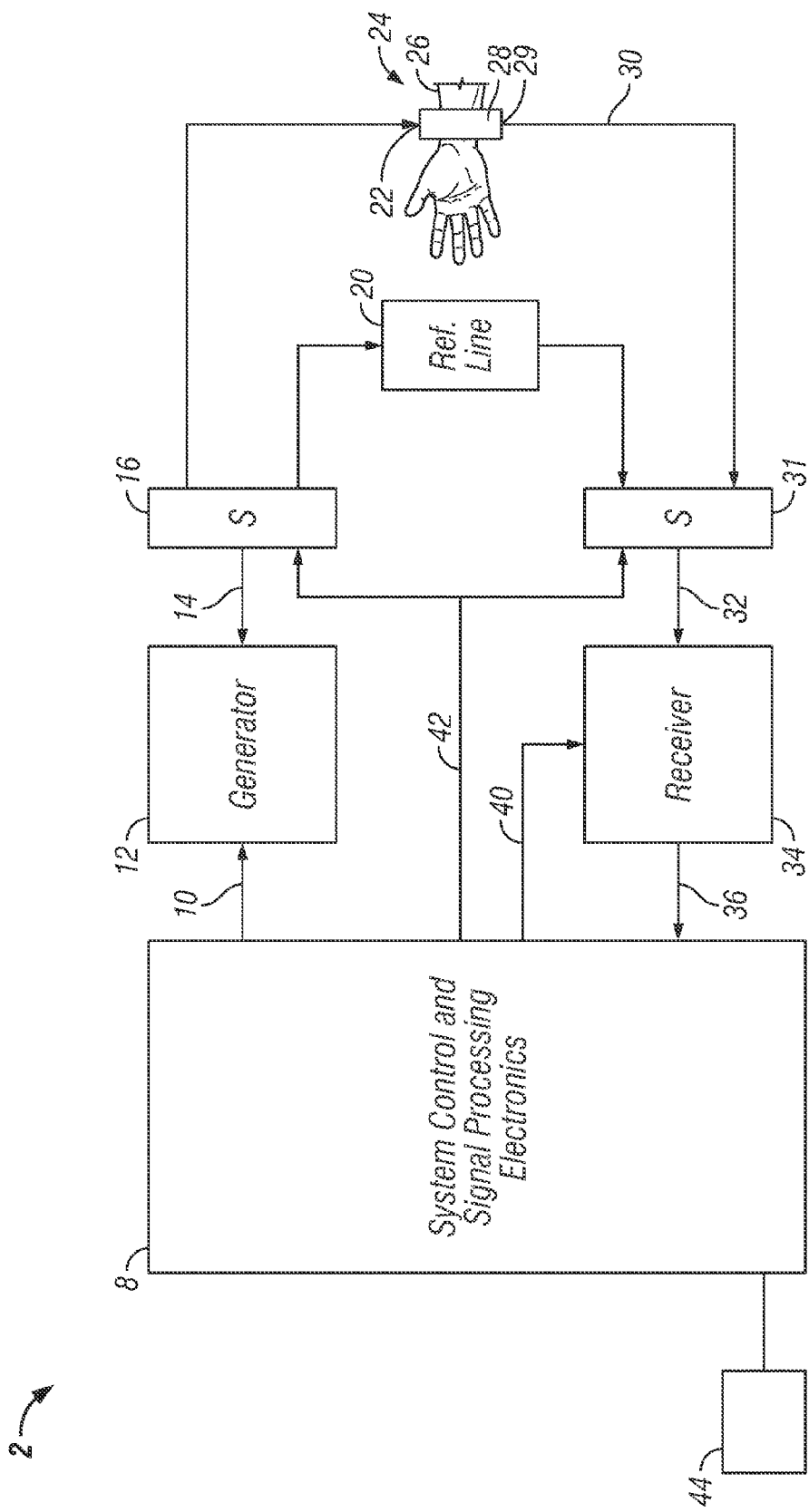
FIG. 1 is a block diagram of an exemplary embodiment of a sensor system.

The Figures described above and the written description of specific structures and functions below are not presented to limit the scope of what Applicant has invented or the scope of the appended claims. Rather, the Figures and written description are provided to teach any person skilled in the art how to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of ordinary skill in this art having benefit of this disclosure. It must be understood that the inventions disclosed and taught herein are susceptible to numerous and various modifications and alternative forms. The use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims.

The present invention is an electromagnetic (EM) sensor and method that permits rapid, precise, accurate, robust, and non-invasive measurement of blood glucose or any other biological parameter that exhibits a unique spectral signature in its complex electrical permittivity within the frequency range from DC or near DC to microwave frequencies. Whereas a primary application of the present invention is focused on the objective of non-invasive measurement of blood glucose, the sensor design and method has wide ranging applicability to a number of important measurement problems in industry, biology, medicine, and chemistry, among others.

The disclosure provides a versatile sensor system and a method of relatively easy extracting of the desired complex permittivity information from the resulting data. The sensor system is particularly well-suited for implementation using low-cost, low-power signal generation and processing electronics. One advantageous feature of the sensor in at least one embodiment is that it can provide a wideband response indicative of both the real and imaginary parts of the complex electrical permittivity in a single measurement channel using amplitude versus frequency information and requires no measurement of phase. Embodiments are also contemplated that incorporate multiple channels of measurement, as well as those that also employ the measurement of signal phase for either single or multiple measurement channels.

The present disclosure maps the information contained in such complex permittivity functions into a signal-space that includes a series of nulls (or valleys) in a frequency domain representation, wherein the frequency location of each null is indicative of the value of the real part of the permittivity at that frequency. The quality factor of the null, as reflected in its depth and width, is indicative of the value of the imaginary part or loss factor of the permittivity.

It will be clear to those trained in the art that a sensor capable of measuring the complex electrical permittivity of a material will also be responsive to its magnetic permeability. In all of the descriptions herein that reference electrical permittivity, such descriptions have like applicability to magnetic permeability. Thus, the disclosure encompasses magnetic permeability as well and the term EM property is used particularly in the claims to reference both electrical permittivity and magnetic permeability.

Figure 4:
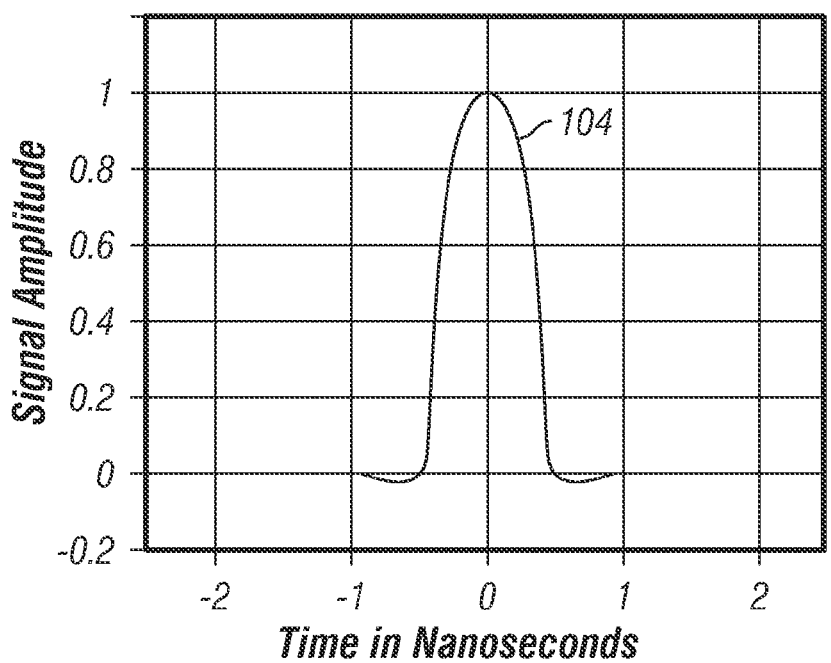
FIG. 4 is a graphical representation of an exemplary ultra-wide band pulse signal.

FIG. 1 is a block diagram of an exemplary embodiment of a sensor system. The sensor system 2 includes various components for controlling, generating, receiving, and processing signals that are dispersed in accordance with the teachings herein. As an exemplary embodiment, a system controller and processor 8 is coupled to a signal generator 12. The controller/processor 8 can control the generator 12 to generate EM energy signals to the system. The generator 12 produces a generator output 14 for testing the material in question. The EM energy signals can be pulsed signals, such as short duration pulsed signals having an ultra-wide bandwidth such as shown in FIG. 4, described below. Alternatively, the EM energy signals can be stepped signals that sequentially expose the material being analyzed to each frequency of interest through a sweep mode. The EM energy can have a wide bandwidth, such as created by amplitude, phase, or frequency modulation, or a combination thereof. Elements which support evanescent waves having a wide bandwidth characteristic are also contemplated and can be included with a sensor and its related assembly. In at least one embodiment, the generator 12 can generate a repetitive sequence of UWB pulses, discussed herein.

Figure 6:
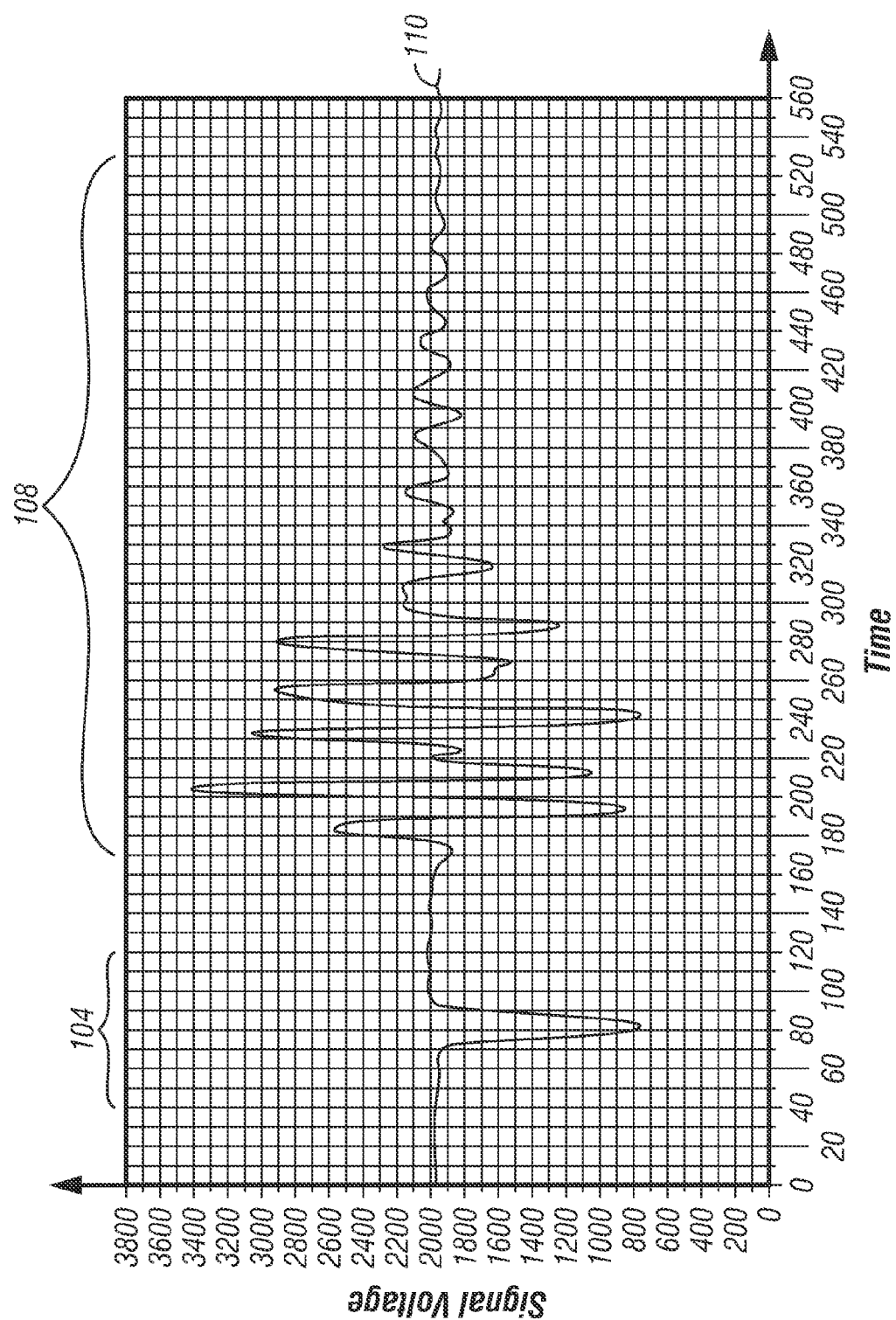
FIG. 6 is a time domain representation of the input and output signals from an exemplary embodiment of the sensor system for the permittivity characteristics such as shown in FIG. 3.

A switch 16 is coupled to the generator 12, and a sensor 28 is coupled to the switch 16 through a sensor input port 22. The function of switch 16 can alternatively be accomplished by a power divider circuit and is included as an effective equivalent. The generator output 14 thus is able to be communicated through the switch 16 to the sensor 28. The sensor 28 is selectively coupled with the material 26 to be analyzed to provide a medium 24 for the EM energy signals. The material 26 can be biological material such as hands, arms, legs, and other parts of a body. Due to the electrical conductivity of such biological material 26, the medium 24 is a dispersive medium. The material 26 can also be non-biological material in some embodiments. The dispersive medium 24 forms a dispersive propagation path that transmits or conveys the received EM energy from the generator 12 to produce, at sensor output 30, response signals through the sensor output port 29. For example, if the generator produces pulses, then the signals at the sensor output 30 will be dispersed pulses such as shown in FIG. 6, described below.

A switch 31 is coupled to the sensor output port 29, and a receiver 34 is coupled to the switch 31. The function of switch 31 can alternatively be accomplished by a power combiner circuit and is included as an effective equivalent. The receiver 34 is coupled to the system controller and processor 8, referenced above. The signals at the sensor output 30 thus are able to be communicated through the switch 31 to the receiver 34. If the receiver 34 uses equivalent time sampling methodology, then the receiver 34 can sample the sensor output having the response signal to produce an acquired sample representation.

The functions performed by controller and processor 8 also comprise system-timing operations, including initiation control signals 10 to the generator 12, generating switch control signals 42 for control of switches 16 and 31, receiver sampling control 40 for control of sample timing in receiver 34, as well as synchronization and interactive system and visual display control.

In at least one embodiment, the signals at the sensor output 30 received by the receiver 34 can be time-sampled to convert the output to a digital format that can be used by the controller and processor 8. If short UWB pulses are used, then to form an accurate digital representation of a narrow-width pulse would ordinarily require that the pulse be sampled at a very high sampling rate, which requires relatively costly electronics. This high cost can be avoided using an equivalent time sampling technique. Rather than sample each pulse at a very high rate, each sample that is needed to provide an accurate representation of a pulse can be acquired from a different pulse in the sequence of pulses received from dispersive medium 24. This allows use of a much slower sampling rate because of the relatively long time duration between pulses. The samples obtained from each pulse are then temporally aggregated to form an acquired sample representation that accurately reproduces a dispersed pulse. This sampling method substantially reduces the cost of the receiver and enables the advantageous use of UWB pulses for material measurements that would otherwise be prohibitively expensive in many applications.

Because the EM energy signals can propagate outside the dispersive medium 24, unwanted reflections of propagating energy from obstructions exterior to the dispersive medium can occur. However, because of the time delay that occurs for propagating energy to exit the dispersive medium, reflect from an obstruction, and return to the sensor, this unwanted reflected energy will arrive at a time that is discernibly later than the time of arrival of the energy that is communicated directly through the dispersive medium. The receiver 34 can discriminate between the late-arriving energy and the energy communicated directly through the dispersive medium. By excluding the late arriving energy from the process, measurement errors arising from unwanted reflections are avoided.

To accurately measure time of arrival and the dispersion caused by the material, as well as to distinguish the dispersed pulse from unwanted later-arriving energy, the UWB pulses of at least one embodiment are generally of very short duration, preferably exhibiting a very rapid rise time, and the time duration between successive pulses must be sufficiently long in comparison to the duration of a pulse. In at least one embodiment, the duration of a pulse can be on the order of a nano-second and the pulse repetition frequency is on the order of a few mega-Hertz (MHz).

Further, the system can provide for time-domain gating in receiving and processing the signals at the sensor output 30, such as UWB pulses. The process of time-gating excludes energy in the received signal that occurs before or after a designated time. This gating can reduce or eliminate sources of error arising from the upstream and downstream reflections of energy from obstructions exterior to the dispersive medium. For example, when the generator 12 produces a repeating sequence of pulses, the time-gate is applied repetitively to exclude unwanted energy arising from each pulse in the sensor output, while accepting the desired energy arising from each pulse. Time gating can also be used to separate the reference line signal from the sensor output signal. The reference line path can be shorter than the measurement path to permit time separation of the measurement and reference signals.

For those embodiments using pulses for input EM energy, the timing of the pulses can be at a regular spacing according to a fixed pulse repetition frequency. Thus, the time intervals between successive pulses will be substantially equal. Alternatively, a pseudo-random or other non-uniform pulse spacing technique can be used. A non-uniform spacing can be selected that will distribute the various frequency components in the pulse sequence over a broad band of frequencies that will appear as a low level noise spectrum to other electronic equipment that could otherwise be affected by stray emissions from the sensor electronics.

Also, the acquired sample representations may be displayed on an output device 44, such as a video monitor, and visually observed to obtain information concerning properties of the substance. For example, the output device 44 may show the amplitude and shape of the received output as a function of time. A time lag between the time when an input energy is transmitted and the time when the output energy is received is caused by the time duration of propagation of the input energy interacting with the material. This time delay can be visually observed and employed to infer properties of the substance. Further, the material interacting with the input energy may cause an attenuation of energy amplitude that can also be visually observed. Moreover, the substance interacting with the energy may cause dispersion of the energy, thereby causing a visibly observable distortion of the shape of the output energy.

Figure 7:
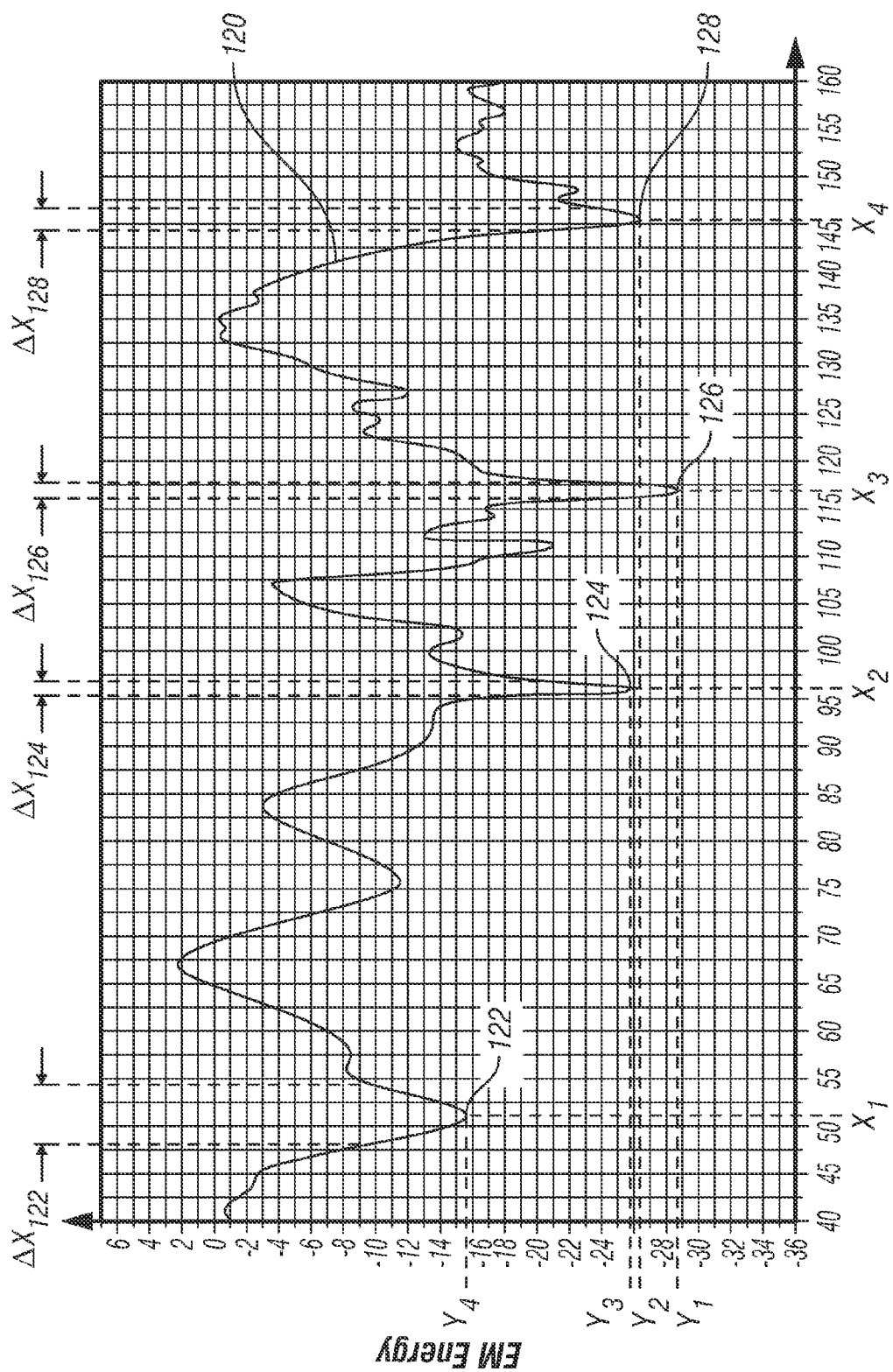
FIG. 7 is a frequency domain representation of the output signal from a transfer function of the time domain representation of FIG. 6.

The output signal can be visually displayed and analyzed in either the time domain or frequency domain. As is known, a signal that varies as a function of time may be represented by a unique signal that varies as a function of frequency. Either representation contains equivalent information. They are mathematically related by a Fourier Transform integral. This integral resolves a continuous-time signal into a continuous-frequency spectrum. Thus, in the alternative to time-domain analysis, it may be convenient to convert the output equivalent-time sampled pulse signal to the frequency domain. The acquired sample representation may be converted to a frequency-domain representation using a Fast Fourier Transform (FFT) algorithm prior to further analysis. The FFT resolves the acquired sample representation into a discrete frequency spectrum. An example is shown in FIGS. 6 and 7 herein and described below.

Further, although applying a Fourier Transform to the output signal enables display and analysis in the frequency domain, other transformations may be applied to the signal captured by receiver 34 to cause other attributes of the signal to be exhibited and analyzed. For example, certain frequency components may be weighted more heavily due to a priori knowledge concerning a desired frequency response of the substance. Likewise, the acquired signal may be time-weighted to emphasize certain temporal features of the signal. As another example, the acquired signal, after being transformed to the frequency domain may be processed by digital filtering before further analysis. Also, the signal can simply be integrated or differentiated prior to or after one or more other transformations are applied. Thus, more generally, the response signal may be processed by performing a transformation of the response signal to produce a resultant signal that is a function of a variable of the transformation.

The aforementioned signal processing of the acquired sample representation obtained in receiver 34 can be performed by the controller and processor 8. Further the controller and processor 8 can use decision algorithms to predict values for the parameter variables of interest. As will be understood controller and processor 8 may include a microprocessor operating under the directions of software that implements the desired algorithms and other functions.

It will often be useful to normalize the spectrum of the signals of the sensor output 30 by the spectrum of the input signals from the generator output 14. The normalization process has the benefit of removing unit-to-unit variations in both the amplitude of the transmitted signals and the gain and frequency response characteristics of the receiver 34. To accomplish the normalization, an attenuated sample of the input signal may be applied directly to the input of the receiver 34 through reference line 20. An input to the reference line 20 can be communicated through the switch 16 that is coupled to the reference line. An output from the reference line 20 can be communicated through the switch 31 that is coupled to the reference line. The receiver 34 and/or system controller and processor can then reproduce an input signal to the sensor 28 and convert the input signal and sensor output to common units for normalization. In at least one embodiment, the input and output of the sensor can be converted from a time domain representation to a frequency domain representation through a Fourier Transform, such as an FFT, to produce a spectral representation of that input signal to the sensor and the output signal from the sensor. When the signals are converted to decibels (dB), normalization involves simple subtraction operations between the input signal and the output signal.

As another example of the output device 44, the device can be coupled with a portable sensor that can be activated to initiate a measurement of one or more desired conditions. An indicator on the device can indicate whether sufficient data is gathered to provide a measurement of the intended condition(s) or whether another attempt is required. Based on an analysis conducted on sufficient data, such as described above, a display on the device can indicate one or more conditions that are being measured, such an analog or digital readout of a numerical value, a sequence of various lights, various colored-coded lights, or other visual indicators of the one or more conditions. In addition to or substitution of one or more visual outputs, in some embodiments, the output device 44 may provide other output, such as audible, tactile, or other sensory output. The output device may include capabilities for transmission, such as Bluetooth® technology, infrared, and other wireless or wired transmission means. The output device 44 can be an alarm indication consisting of a blinking light, a buzzer or similar indication to communicate to a user that a predetermined condition of the material under test has been reached or exceeded, requiring some response on the part of the user. The transmission can be coupled with a computer, monitoring system, pager, or other devices that, for example, can alert third parties of an adverse or other sensed condition, especially if the user is unable to seek help or otherwise respond or communicate.

Figure 2:
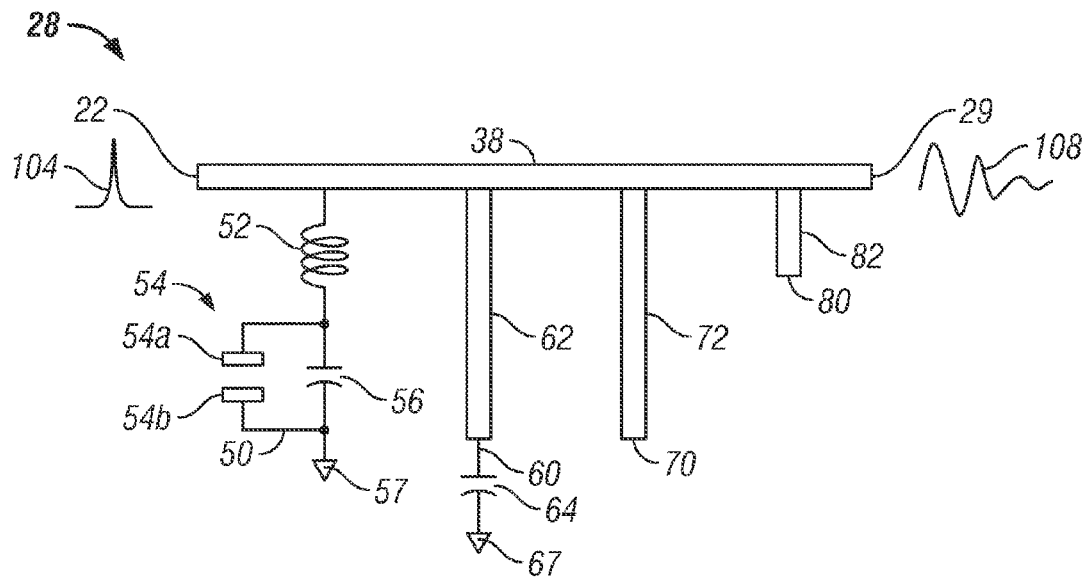
FIG. 2 is schematic representation of an exemplary embodiment of the sensor.

FIG. 2 is schematic representation of an exemplary embodiment of the sensor. In general, the sensor includes a transmission line that accepts an input electrical signal in the form of a propagating EM wave. The propagation of the wave along the transmission line is affected by the presence of one or more resonant circuits that are connected in parallel to the transmission line. One or more of the resonant circuits has at least a portion of the circuit composed of one or more lumped element circuit components, distributed element circuit components, or a combination thereof, whose electrical properties are changed by coming in contact with or in close proximity to the object or material that is to be measured.

The sensor 28 includes an input port 22 and an output port 29. The input port 22 and the output port 29, through which the EM energy is transmitted to the dispersive medium 24 and received from the dispersive medium, respectively, can include or incorporate a probe, loop, aperture, or other transmitting or receiving element. The sensor 28 further includes a signal transmission line 38. The transmission line 38 can be formed from a variety of configurations, including a microstrip transmission line (as shown), and other transmission line structures, such as slotline, stripline, twin-line, co-planar waveguide, dielectric waveguide, and the like, used singularly or in combination. In particular, a transmission line which can support a true transverse electromagnetic (TEM) wave (such as stripline) may have some advantage in some applications for the main thru-line signal path over a structure which only supports a quasi-TEM mode of propagation (such as microstrip). A transmission line which supports a true TEM mode will exhibit less dispersion than a mode having quasi-TEM propagation. Transmission lines of both types are useful within the scope of this invention, as will be evident to those skilled in the art, and both types are included. Transmission lines which support only transverse electric or transverse magnetic also have useful properties within the scope of the invention and are included in the consideration of the description of operation of the sensor and in the various resulting claims. In at least one embodiment, the transmission line 38 is protected from effects of the material to be measured, such as not being in contact or close proximity.

The sensor 28 further includes a plurality of parallel-connected resonant circuits or "stub" elements coupled at various points along the transmission line 38. The number can vary from one to many and the schematic showing four stub elements is only exemplary and not limiting. The stub elements include frequency sensitive components of either lumped element circuit components or distributed element circuit components, or a combination thereof, depending on the resonant frequency or band desired for a given stub. Each stub is designed to present an effective parallel short-circuit connection to signal ground along the main transmission line within one or more desired bands of frequency and to appear as an open circuit or high-impedance value at frequencies outside its selected bands of measurement. For each stub, at least one component or one sensitive area or zone is provided such that, when the parallel connected resonant circuit or stub is coupled by means of contact or close proximity to the tissue or other material 26 being measured, the circuit value of the stub is affected by the electrical permittivity of said tissue or material under test.

More particularly, a lumped element resonant circuit 50 is coupled to the transmission line 38. The lumped element resonant circuit 50 can include one or more lumped element circuit components in series or in parallel to each other or a combination thereof. For example, the lumped element circuit components can include an inductor 52 in series with a capacitor 56 in parallel with a responsive circuit component 54. The responsive circuit component 54 can be a circuit component that can be affected by contact with or close proximity to (for example, one inch or less) the material to be analyzed. In at least one embodiment, the responsive circuit component can be a capacitive component having a capacitance establishing EM fields between plates of the capacitive component that are affected in their field lines (and therefore capacitance) by contact with or proximity to the material. As the capacitance changes with the material, the resonant frequency changes for the resonant circuit. Changes in the resonant frequency can help determine whether the characteristic being measured is present in the material. The lumped element resonant circuit 50 includes a grounding component 57. As described below, when a frequency passing through the transmission line matches the resonant frequency of the resonant circuit as affected by the material being measured, then the resonant circuit creates a short-circuit condition through the ground at that frequency.

As another example, a combination lumped element and distributed element resonant circuit 60 is also coupled to the transmission line 38. A distributed element circuit component 62 is shown coupled to the transmission line 38 and can include distributed properties of a distributed resistor, capacitor, inductor, or a combination thereof. The distributed element 62 can be a transmission line whose EM fields are responsive to material in contact with or in proximity to the transmission line 62. A lumped element circuit component, shown for example, as a capacitor 64, is coupled to the distributed element circuit component 62. The resonant circuit 60 further includes a ground 67 to provide a short-circuit path at the resonant frequency of the resonant circuit. The order of the distributed element circuit component 62 and the lumped element circuit component, shown for example as the capacitor 64, can be changed.

Other exemplary resonant circuits, such as a distributed resonant circuit 70 and a distributed resonant circuit 80, are also shown coupled to the transmission line 38. The resonant circuit 70 can include a distributed element circuit component 72. The resonant circuit 80 can include a distributed element circuit component 82. Each of the distributed element circuits 70, 80 may be configured without a specific grounding component, as in distributed element circuits 50, 60. Nevertheless, the size and nature of the distributed element circuits 70, 80 and resulting resonant frequencies in conjunction with the material to be analyzed may cause the distributed element circuits 70, 80 to effectively function as a short-circuit at such resonant frequencies. For example, the distributed element circuits 70, 80 can include a transmission line 72, 82 whose EM fields are responsive to material in contact with or in proximity to the transmission line, and may have properties of a distributed resistor, capacitor, inductor, or a combination thereof.

Other elements and arrangements of elements are possible and contemplated and the above examples of resonant circuits are nonlimiting. Further, the number of resonant circuits from one to many can vary depending on the characteristic(s) being measured, the number of frequencies needed to determine the characteristic(s), the degree of accuracy desired for the characteristic(s) and other factors.

As referenced above, the series resonant condition for each of the shunt-connected resonant circuit 50, 60, 70, 80 is such that an effective short-circuit condition is created for the main transmission line 38 at a frequency that is determined in part by the electrical properties of the tissue or other material 26 being measured. The short-circuit condition presented to the main transmission line 38 causes an output signal 108 measured at output port 29 to exhibit a near zero or null value at the frequency for which the given resonant circuit is in its resonant condition.

Those skilled in the art can chose circuit component values, so that the resonant frequency condition for each of the resonant circuits 50, 60, 70, 80 can be caused to occur within predetermined different windows or narrow bands of frequencies for a given permittivity profile expected of the tissue or material being measured. Such values may depend on electrical lengths of the various circuit components, the physical dimensions of the transmission lines, the electrical properties of the circuit board material upon which the transmission line is fabricated and other components and real world losses in a given circuit. It is also apparent that many resonant circuit configurations for the various types of transmission lines are possible, including structures not expressly presented here, but which fall within the scope of the present disclosure.

Further, in at least some embodiments, a special class of materials, known as "metamaterials" can be used for both the implementation of the resonator elements and for improving the coupling of electromagnetic energy into the material to be analyzed, such as biological tissues. Metamaterials are a class of complex materials in which the permittivity or the permeability or both can possess negative values for a range of desired frequencies. These materials exhibit properties that can be beneficial for the implementation of the sensor for glucose measurement. In particular, these so-called left handed or backward wave materials can be used to reduce the physical size of resonator elements while still achieving a low frequency resonant response. The metamaterials can be used to lower a resonant frequency of a resonant circuit, which can be advantageous in measuring low frequency output signals from the material to be analyzed. Likewise, certain geometric patterns can be utilized in the ground plane beneath the resonating elements to increase the depth of penetration into the tissues and increase the sensitivity of the sensor.

Figure 3:
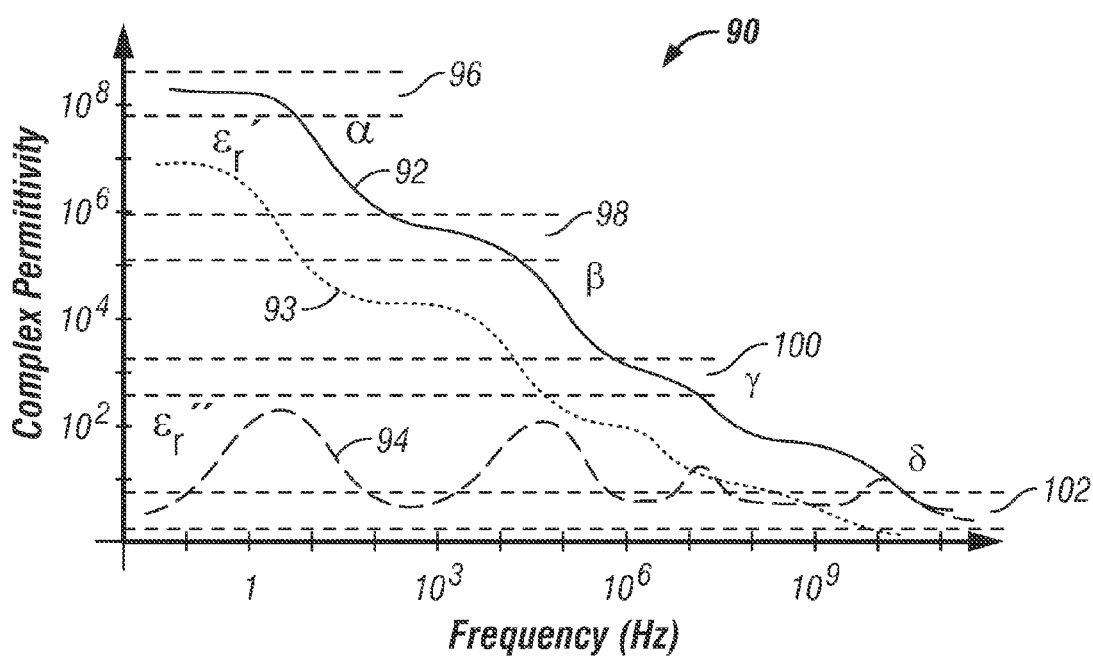
FIG. 3 is a frequency domain representation of electrical permittivity properties of biological tissues.

FIG. 3 is a frequency domain representation of electrical permittivity properties of biological tissues. Many materials, particularly biological tissues, have permittivity properties that are strong functions of frequency. Research has shown that a generalized graph of the EM energy (here, complex electrical permittivity) of biological tissues can be represented as illustrated in FIG. 3. The graph maps a representative curve of permittivity, with frequency as the X-axis and the permittivity as the Y-axis in logarithmic values. The complex permittivity shows the real component curve 92 of the permittivity as a solid line $\in_r'$, and the imaginary component curve 94 of the permittivity as a dashed line $\in_r''$. As shown, the permittivity is dependent on the frequency ω.

In the representative chart, four exemplary output signal dispersion regions of permittivity relative to frequency are labeled as α, β, γ, δ in successive order as the real permittivity component cascades in a generally downward slope to lower levels of permittivity with increasing frequency. Further, for this example, relatively narrow bands of permittivity for a range of frequencies are nominated as first permittivity region 96 above the α-dispersion region, second permittivity region 98 between the α- and β-dispersion regions, third permittivity region 100 between the γ- and δ-dispersion regions, and fourth permittivity region 102 below the δ-dispersion region. The regions can be varied and the above examples are non-limiting. For example, other regions can be selected above and below the exemplary regions; the range or ranges of the regions can be varied individually or collectively from one characteristic to another; the number of regions can be varied, and other variances depending on the curve of the characteristic to be mapped and the sensitive portions of the response to particular characteristic being measured.

In general, a known characteristic can be measured and mapped to establish a characteristic signature such as shown in curve 92. The curve, for example, can be based on the EM properties of permittivity or permeability of the known characteristic of the material. Other signatures, such as curve 93, for other characteristics, such as a different permittivity response to frequencies caused by a change in the material or its composition, can be measured and mapped. Then, testing can be performed on the same material under conditions having unknown characteristics or a different material than was used to establish the signature and having unknown characteristics, and the results for the unknown characteristics correlated to the signature for the known characteristic. In the example, one or more of these regions 92, 98, 100, 102 can encompass data related to the characteristic shown in a particular portion of a curve being tested by the sensor 28 with the resonant circuits 50, 60, 70, 80. Stated differently, if one or more resonant circuits are tuned to become resonant within a range of frequencies that have been mapped to indicate a certain permittivity at such resonant frequencies, then the data revealed at those resonant frequencies individually with one resonant circuit or collectively using more than one resonant circuit can be used to indicate a characteristic of the material that is being measured. The results can show the location and the amplitude of nulls or near zero values along the frequency axis, as well as width of descending and ascending curves associated with such values, that occurred at the shunted resonant frequencies can correspond to properties that indicate a characteristic of the material.

For example, for the resonant circuits shown in FIG. 2, the lumped element resonant circuit 50 can be tuned with a resonant frequency in combination with a material to be tested to provide a sensor response at very low frequencies. Such low frequencies are shown, for example, at the first permittivity region 96 in FIG. 3 above the α-dispersion region. Such low frequency response can be important in measuring properties, for example, of biological tissues. The combination lumped element and distributed element resonant circuit 60 can be tuned to provide a sensor response at the second permittivity region 98 between the α-dispersion region and the β-dispersion region. The distributed resonant circuit 70 can be tuned to provide a sensor response at the third permittivity region 100 between the β-dispersion region and the γ-dispersion region. The distributed resonant circuit 80 can be tuned to provide a sensor response at the fourth permittivity region 102 below the δ-dispersion region.

Figure 5:
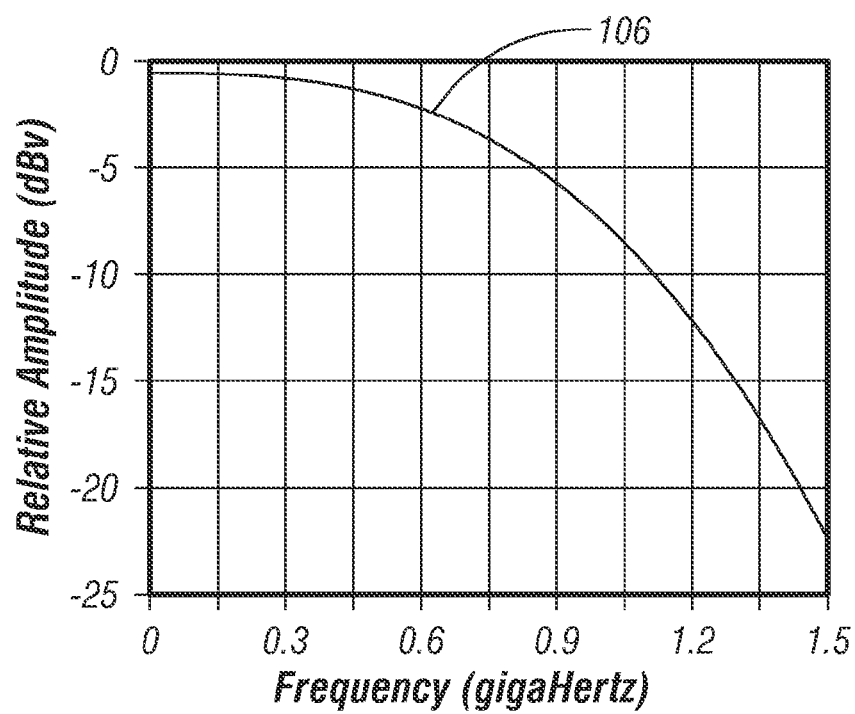
FIG. 5 is the frequency domain representation of the pulse in FIG. 4.

FIG. 4 is a graphical representation of an exemplary ultra-wide band pulse signal. FIG. 5 is the frequency domain representation of the pulse in FIG. 4. The figures will be described in conjunction with each other. The particular pulse shown in FIG. 4 is a Gaussian amplitude-weighted sin(x) over x pulse, representative of a general class of UWB pulses, but not the only type of pulse that may be employed in the present invention. (Note that in FIG. 4, both negative and positive values appear along the horizontal axes as shown, with time t=0 coinciding with the peak of the pulse. This is consistent with standard mathematical analysis methods, although other coordinate orientations can be employed.) In at least one embodiment, the generator 12, shown in FIG. 1, can produce a series of short duration pulses. An inverse relationship exists between the time duration of a pulse of energy and the frequency bandwidth of the energy spectrum of the pulse. The shorter the duration of the pulse, the wider will be the band of frequencies of energy comprising the pulse.

The bandwidth of such pulses can be approximated according to the following equation:

$$BW = \frac{.35}{t_r}$$

where BW is the bandwidth of the pulsed signal in Hertz and $t_r$ is the rise or fall time of the signal in seconds. For example, rise or fall times on the order of 100 ps will produce an approximate signal bandwidth of 3.5 GHz.

Therefore, the frequency spectrum of a narrow input pulse, such as is shown in FIG. 4, will resemble the broad spectrum shown in FIG. 5. A sufficiently narrow UWB pulse 104 will exhibit a broad frequency domain 106 of energy that interacts over a desired frequency range with the dispersive medium 24 provided via the sensor 28 and the material 26, shown in FIG. 1. This broadband energy distribution in the dispersive medium 24 interacts with, and is dispersed by, the material 26. This dispersion can be a function of frequency, the shape and size of the dispersive medium, and the characteristics of the material.

Dispersion affects the shape, duration, phase, and time of arrival of the energy pulses as output signals from the sensor, where the dispersed pulses are received by the receiver 34 in FIG. 1. Thus, the dispersive medium 24 forms a dispersive channel with one or more frequency responses of substantial amplitude over a broad spectrum.

FIG. 6 is a time domain representation of the input and output signals from an exemplary embodiment of the sensor system for the permittivity characteristics such as shown in FIG. 3. The time domain output signal 108 of FIG. 2 is shown in more detail in FIG. 6. The graph maps a representative curve of signal voltage as the Y-axis as a function of time for the X-axis. The time domain output curve 110 represents a replication of the input signal 104, communicated to the receiver through reference line 20, and a time domain representation of the dispersed output signal 108. In this example, the input signal 104 is a well defined periodic signal having an ultra-wide bandwidth by virtue of its very rapid transient characteristic. As described in FIG. 1, the input signal 104 can be received with the output signal 108 by the receiver 34 to provide for normalization adjustments. As this input signal 104 propagates along the sensor transmission line 38, shown in FIG. 2, the signal is dispersed in time according to the different time delays experienced by the various frequencies that make up the initial bandwidth of the input signal. The dispersed output signal 108 becomes highly distorted by the velocity dispersion effects according to the well known theory of non-linear phase response transmission lines.

Whereas the frequency domain information produced according to the present disclosure allows for determination of the complex permittivity versus frequency response of the material under test, there are applications for which the actual computation of permittivity is not required or desirable. In some embodiments, it may be preferable to extract the desired composition information (such as blood glucose concentration) directly from the signal itself without computing permittivity values.

FIG. 7 is a frequency domain representation of the output signal from a transfer function of the time domain representation of FIG. 6. Whereas the time domain output signal 108 contains all the information available from the sensor, it may be advantageous to convert the signal from a time domain representation to a frequency domain representation. Such conversion can be made by using a suitable transform algorithm, such as a Fast Fourier Transform (FFT), and thereby produce a spectral frequency domain representation of the sensor output signal 108 as seen in FIG. 7 with a resulting frequency domain output curve 120. The graph maps a representative curve of EM energy (here, permittivity, expressed in decibels "dB") as the Y-axis as a function of frequency for the X-axis.

The curve 120 exhibits a series of nulls or dips in the signal amplitude versus frequency. For example, the nulls include a first null 122 at point $X_1$ along the X-axis, a second null 124 at point $X_2$, a third null 126 at point $X_3$, and a fourth null 128 at point $X_4$. These points $X_1$, $X_2$, $X_3$, and $X_4$ where the signal nulls occur correspond to the frequency values for which the parallel connected circuit components to the transmission line 38, shown in FIG. 2, have become resonant and therefore the signal effectively shorted, as determined by the physical properties of the circuit components and the permittivity properties of the material being measured. The location of each null along the frequency axis is indicative of the real part of the permittivity of the tissue at that frequency, whereas the depth, width, or a combination thereof of each null is indicative of the corresponding imaginary part of the permittivity. While other dips in the curve are shown, in many such instances, these other dips are not true nulls, but are the result of reflections, standing waves, harmonics, and other undesirable results under real world conditions. Thus, in some embodiments, it is advantageous to select certain ranges of frequencies along the X-axis to look for expected nulls. The ranges can be selected by a priori knowledge of the characteristic(s) being measured.

As a given null moves to the right or left along the frequency axis, it indicates a decrease or increase in value of the real part of the permittivity, respectively. As a given null depth along the Y-axis increases or decreases, and as it increases or decreases in width, it indicates the imaginary portion of the permittivity. The width of the nulls can be measured with some appropriate standard applied to the nulls before and after the lowest point of the null. For example and without limitation, an appropriate standard could include a point in the fall and rise of the null, such as the EM energy along the Y-axis measured at 6 dB (or some other dB or metric) before the lowest point of the null along the X-axis to the EM energy along the Y-axis measured at 6 dB after the lowest point of the null along the X-axis.

For example, the null 122 can have an EM energy $Y_4$ at frequency $X_1$. The frequency $X_1$ can indicate a resonant frequency for a given characteristic that created a short-circuit condition from the resonant circuits, such as resonant circuit 50, described above. The width $\Delta X_{122}$ of the null 122 can be established between 6 dB before frequency $X_1$ and 6 dB after frequency $X_1$. In a similar manner, the null 124 has an EM energy $Y_3$ (lower than null 122) at frequency $X_2$. The width $\Delta X_{124}$ of the null 124 can be established between 6 dB before frequency $X_2$ and 6 dB after frequency $X_2$. The null 124 has a narrower width than the null 122. A similar comparison can be made for null 126 having an EM energy $Y_1$ at frequency $X_3$ and a width of $\Delta X_{126}$, and for null 128 with an EM energy $Y_2$ at frequency $X_4$ and a width of $\Delta X_{128}$. For a curve that has one or more abrupt changes within the selected range before or after the null, such as the dip after null 128 in the exemplary curve in FIG. 7, some adjustments may be useful in filtering out such abrupt changes. Adjustments can include, without limitation, narrowing the standard (for example, from 6 dB to 3 dB) before and after the nulls being measured to exclude the abrupt change, doubling a width (measured by the standard) of one side of the curve from the null that does not have the abrupt change (such as in FIG. 7, doubling the width from the 6 dB before the null 128) to obtain a total width before and after the null, or other processing adjustments and criteria.

Figure 8:
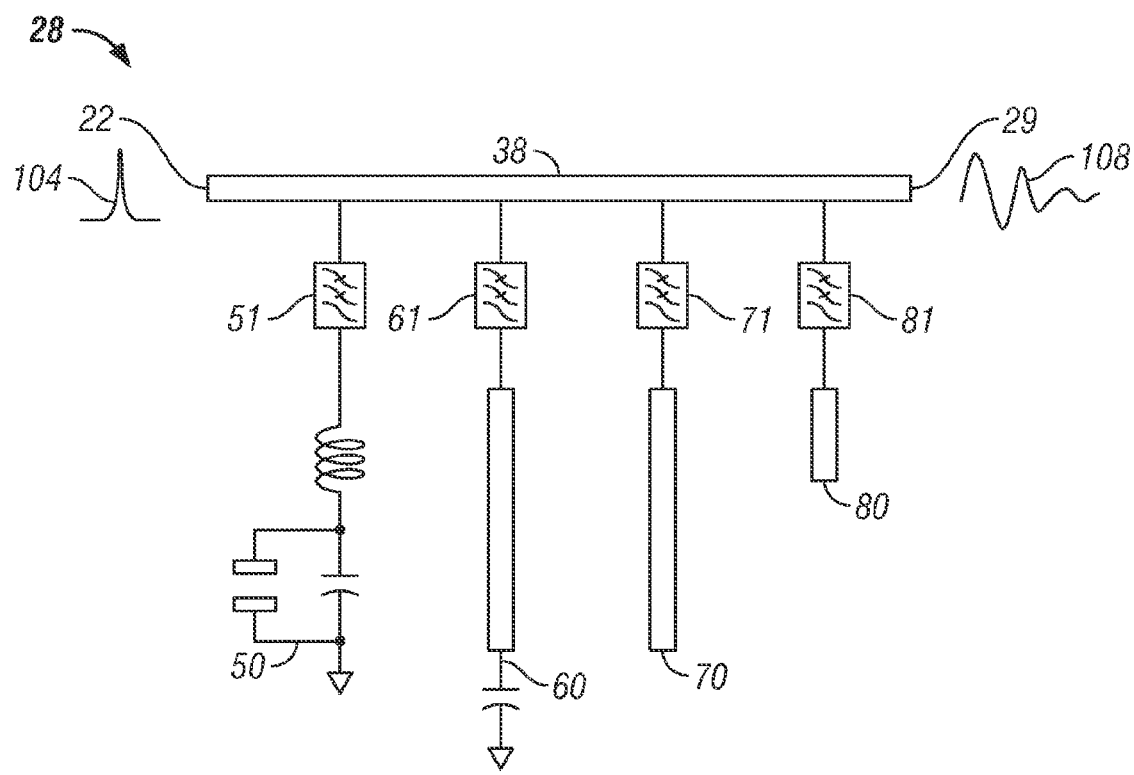
FIG. 8 is a schematic representation of another embodiment of the sensor showing an arrangement of individually tuned filter elements connected between the main transmission path and the resonant circuits.

FIG. 8 is a schematic representation of another embodiment of the sensor showing an arrangement of individually tuned filter elements connected between the main transmission path and the resonant circuits. The sensor 28 shown in FIG. 8 is similar to the sensor in FIG. 2 and similar components are similarly numbered. The sensor 28 includes a transmission line 38 with one or more resonant circuits 50, 60, 70, 80 coupled thereto. The resonant circuits, having lumped element and/or distributed element circuit components, can effectively shunt the spectral components of the input signal 104 to ground at various resonant frequencies based on the input signal as it is dispersed along the transmission line 38 to produce the output signal 108 that is affected by the material to be analyzed, as described above. In addition, the embodiment of FIG. 8 includes one or more tuned filter elements 51, 61, 71, 81 connected between the transmission line 38 and the resonant circuit components. The tuned filter elements each can define only one series resonant condition for its resonant circuit over the operating frequency range of the sensor 28. For example, the filter elements can be low-pass filter elements allowing a fundamental frequency to pass while blocking harmonic frequencies and other unwanted resonant conditions that affect the output signal 108.

Figure 9:
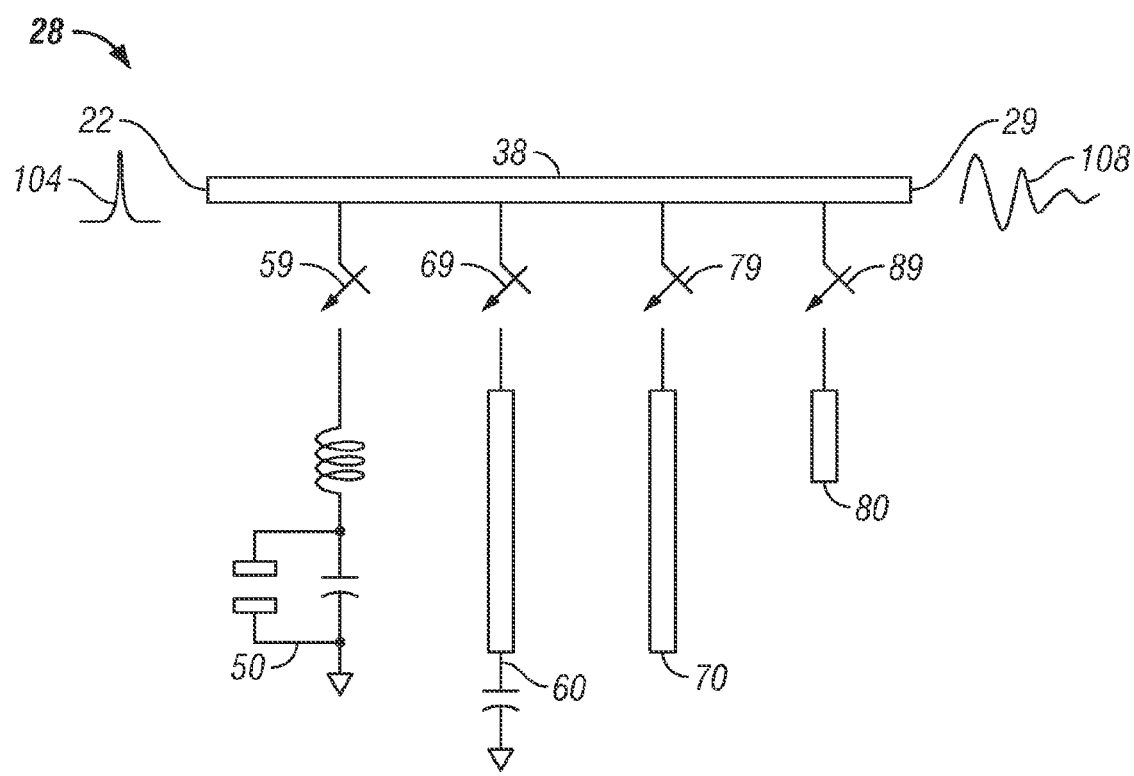
FIG. 9 is a schematic representation of another embodiment of the sensor showing an arrangement of individually controllable switching elements that function to selectively connect or disconnect the resonant circuits.

FIG. 9 is a schematic representation of another embodiment of the sensor showing an arrangement of individually controllable switching elements that function to selectively connect or disconnect the resonant circuits. The sensor 28 shown in FIG. 9 is similar to the sensor in FIGS. 2 and 8 and similar components are similarly numbered. The sensor 28 includes a transmission line 38 with one or more resonant circuits 50, 60, 70, 80 coupled thereto. The resonant circuits, having lumped element and/or distributed element circuit components, can effectively shunt the input signal 104 to ground at various resonant frequencies based on the input signal as it is dispersed along the transmission line 38 to produce the output signal 108 that is affected by the material to be analyzed, as described above. In addition, the embodiment shown in FIG. 9 includes switches 59, 69, 79, 89 for the resonant circuits. The switches can be controlled to change an operational state of the resonant circuit and allow a resonant condition to be created through the resonant circuit in time sequence rather than all substantially at the same time. For example, when pulses are used, the switch 59 can close to allow the resonant circuit 50 to shunt at the proper frequency for one or more of the pulses, while switches 69, 79, 89 remain open. Similarly, the other switches 69, 79, 89 can be closed at various times to allow the resonant conditions for the respective resonant circuits for other pulses. The number of switched resonant circuits can vary from none to all.

Figure 10:
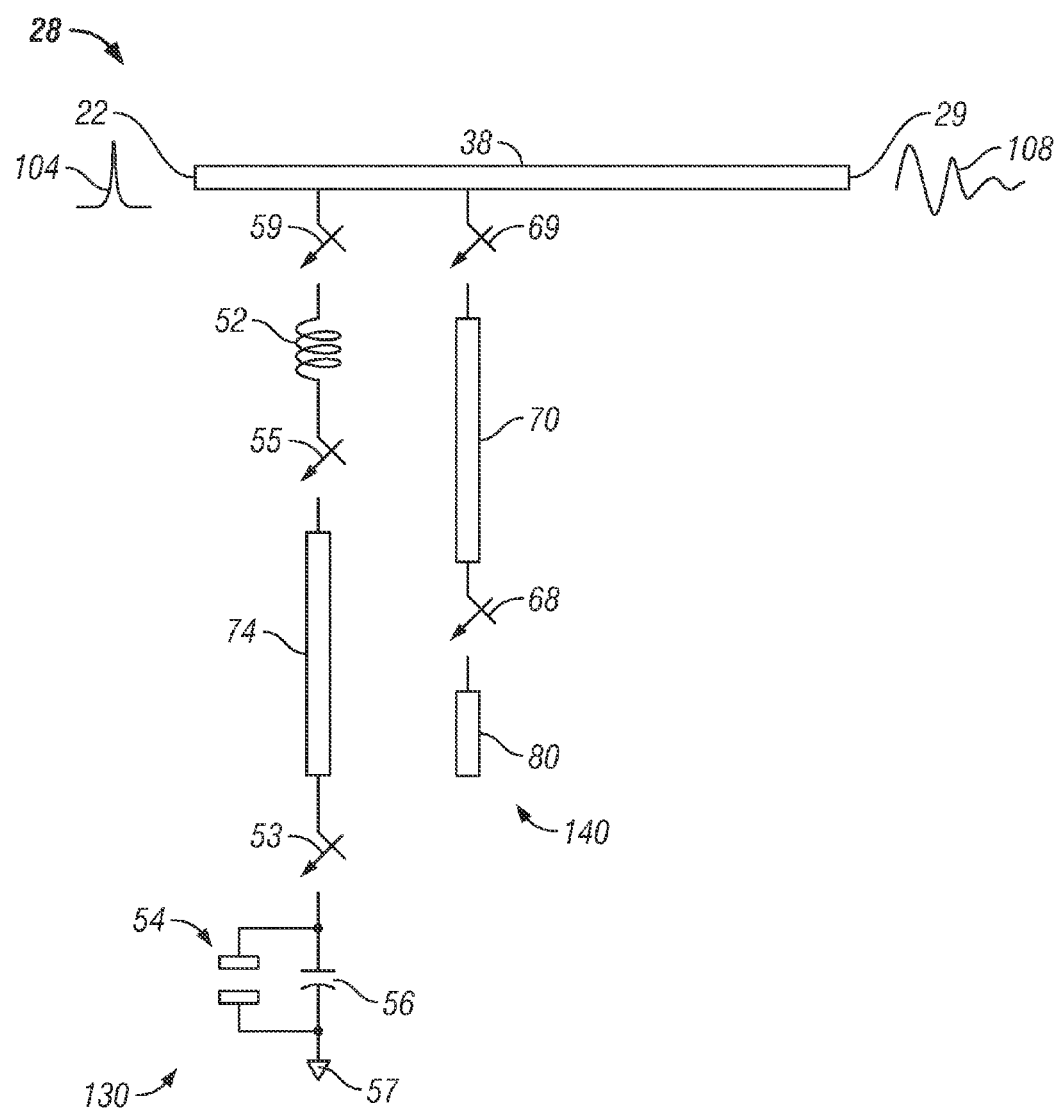
FIG. 10 is a schematic representation of another embodiment of the sensor showing one or more resonant circuits for which the resonant frequency of the circuit can be modified by a suitable switching in or out of lumped element circuit components or distributed element circuit components.

FIG. 10 is a schematic representation of another embodiment of the sensor showing one or more resonant circuits for which the resonant frequency of the circuit can be modified by a suitable switching in or out of lumped element circuit components or distributed element circuit components. The sensor 28 shown in FIG. 10 is similar to the sensor in FIGS. 2, 8, and 9 and similar components are similarly numbered. The sensor 28 includes a transmission line 38 with one or more resonant circuits 50, 60, 70, 80 coupled thereto. The resonant circuits, having lumped and/or distributed element circuit components, can effectively shunt the input signal 104 to ground at various resonant frequencies based on the input signal as it is dispersed along the transmission line 38 to produce the output signal 108 that is affected by the material to be analyzed, as described above. In addition, the embodiment shown in FIG. 10 includes switches for one or more resonant circuits 50, 130. The switches can be coupled between the resonant circuits 130, 140 and the transmission line 38, as well as within the circuits, such as between the circuit components 52, 74 of the resonant circuit 50. The switches between the circuit components can change the operational state of the circuit components of the resonant circuit and therefore change the resonant frequency of the resonant circuit. For example, a switch 59 can be coupled between the resonant circuit 130 and the transmission line 38, switch 55 can be coupled between the inductor 52 and the distributed element 74, and switch 53 can be coupled between the distributed element 74 and the capacitor 56 and the responsive circuit component 54. The switch 59 can control the ability of the resonant circuit 50 or portions thereof to respond to a resonant frequency. The one or more switches 53, 55 can allow portions of the resonant circuit 130 to be switched on and off when the switch 59 is switched on. Thus, the switches 53, 55 can change the resonant conditions of the resonant circuit 130.

Further, the figure shows switches that are arranged in series with the components. It is to be understood that variations of the illustration are contemplated. For example, to switch off an upstream component such as component 52 and switch on components downstream, such as components 74, 56, the system could use a short circuit link around component 52 with a switch installed in the short-circuit. The switch 59 and 55 would be opened to disconnect the component 52 and the switch on the short-circuit closed to short around the component 52.

In at least one embodiment, the resonant circuit 130 can be designed to encompass the various dispersion regions desired to provide the data to characterize the condition to be measured. Thus, one resonant circuit could be coupled to the transmission line 38 with the ability to be configured with multiple resonant frequencies depending on the circuit components switched into the circuit for operation at a given time. The one resonant circuit could function as multiple resonant circuits.

In other embodiments, the capability for multiple resonance frequencies could be divided into more than one resonant circuit. For example, the sensor 28 in FIG. 10 could also include a resonant circuit 140 having one or more circuit components, such as distributive element circuit components 70, 80. A switch 69 can be coupled between the resonant circuit 140 and the transmission line 38, and a switch 68 coupled between the distributive element circuit components 70, 80.

Figure 11:
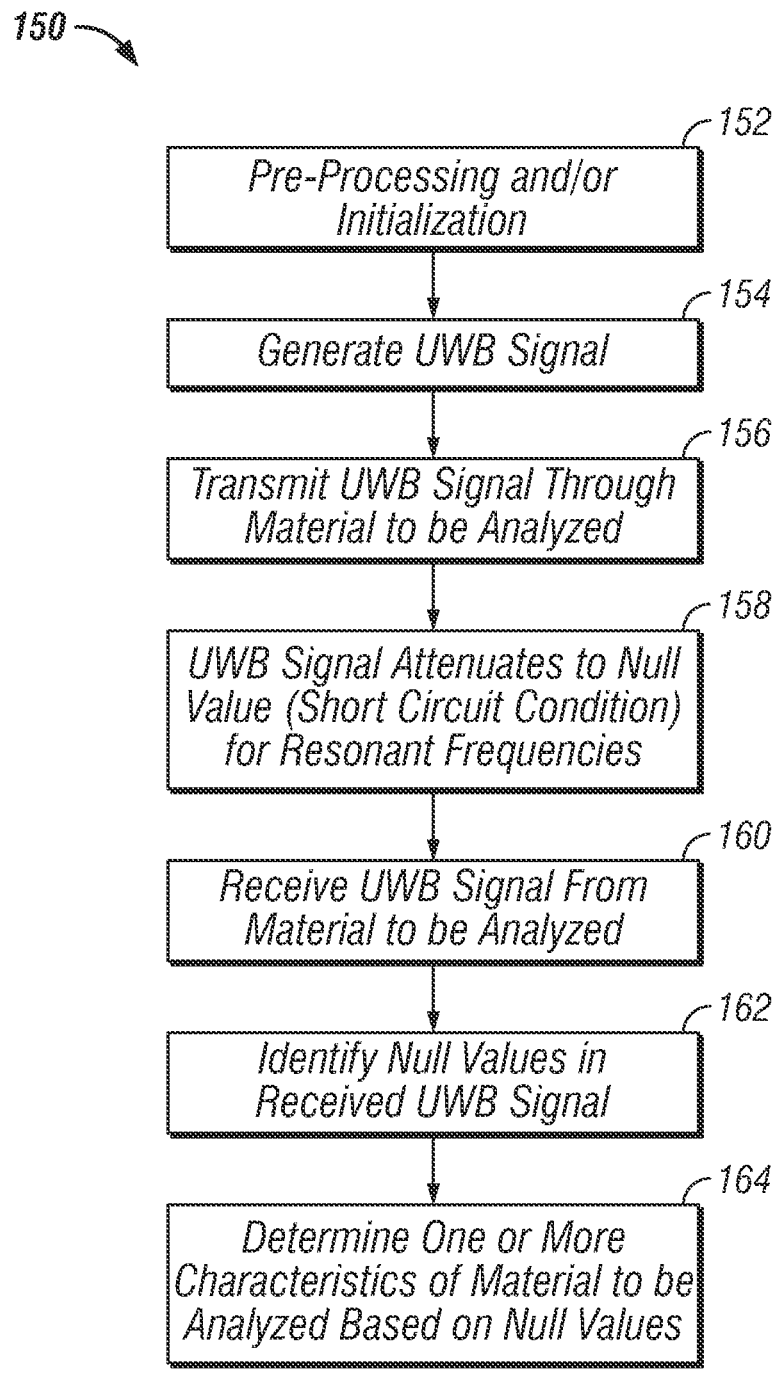
FIG. 11 is a flowchart of a method that may be used for the sensor to determine one or more characteristics of a material to be analyzed.

FIG. 11 is a flowchart of a method that may be used for the sensor to determine one or more characteristics of a material to be analyzed. Various and nonlimiting embodiments of the ultra-wideband sensor have been discussed thus far in terms of several specific implementations for using an ultra-wideband signal to determine one or more characteristics of a material, such as a biological material. FIG. 11 provides general guidelines in the form of a flow chart 150 for a nonlimiting method to determine the one or more characteristics. Note that although the flowchart 150 contains a number of discrete functional blocks, one or more of these blocks may be removed from the flowchart 150, and/or one or more other blocks may be added to the flowchart 150, without departing from the scope of the disclosed embodiments. In addition, one or more of the blocks may be combined with one or more other blocks or divided into multiple smaller blocks as needed without departing from the disclosed embodiments. Furthermore, although the blocks are displayed in a particular order, those having ordinary skill in the art will recognize that one or more blocks may be performed out of sequence and/or simultaneously with one or more other blocks as needed.

The flowchart 150 begins generally at block 152, where any necessary pre-processing and/or initialization is performed. It is assumed at this point that the material to be analyzed has been coupled to or otherwise brought in close proximity with the ultra-wideband sensor. The ultra-wideband sensor, as explained above, includes a transmission line that has one or more resonant circuits connected in parallel to the transmission line. One or more of the resonant circuits has at least a portion of the circuit composed of one or more lumped element circuit components, distributed element circuit components, or a combination thereof, whose circuit values are affected by contact with or close proximity to the material to be analyzed. These one or more lumped element circuit components, distributed element circuit components, or combination thereof, function to cause the resonant circuits to enter a low-impedance or short-circuit condition at a particular resonant frequency that is specific to that resonant circuit, as discussed above. In general, each resonant circuit has a different resonant frequency, but it is possible in some embodiments for two or more resonant circuits to have the same or nearly the same (e.g., within ±10%) resonant frequency.

At block 154, an ultra-wideband signal of electromagnetic energy is generated that is then dispersed through the material to be analyzed at block 156 via the sensor 28 shown in FIG. 1 (e.g., by connecting the ultra-wideband signal to the transmission line of the sensor 28). As the ultra-wideband signal propagates through the transmission line, the resonant circuits, and the material to be analyzed, the signal is attenuated at block 158 toward one or more null values, or dips in the signal's amplitude, for frequency components that are at or within a certain range (e.g., ±10%) of the resonant frequencies of the one or more resonant circuits. Generally, little or no attenuation is expected to be seen for frequency components of the signal that are not at or within a certain range of the resonant frequencies.

At block 160, the ultra-wideband signal is received (i.e., sampled) from the material to be analyzed, and the null values in the signal resulting from the resonant frequencies are identified at block 162. At block 164, the null values are used to determine one or more characteristics of the material to be analyzed. Such a determination may be performed based on, for example, a comparison of the received nulls with the nulls from a previously obtained baseline signal, the current number of nulls versus the total number of available nulls, the location of each null, the depth of the null, and the like. Once the one or more characteristics of the material is analyzed, this information may be used to monitor and/or alert a user as to the status of the material to be analyzed, as described with respect to FIG. 16 below.

Figure 12:
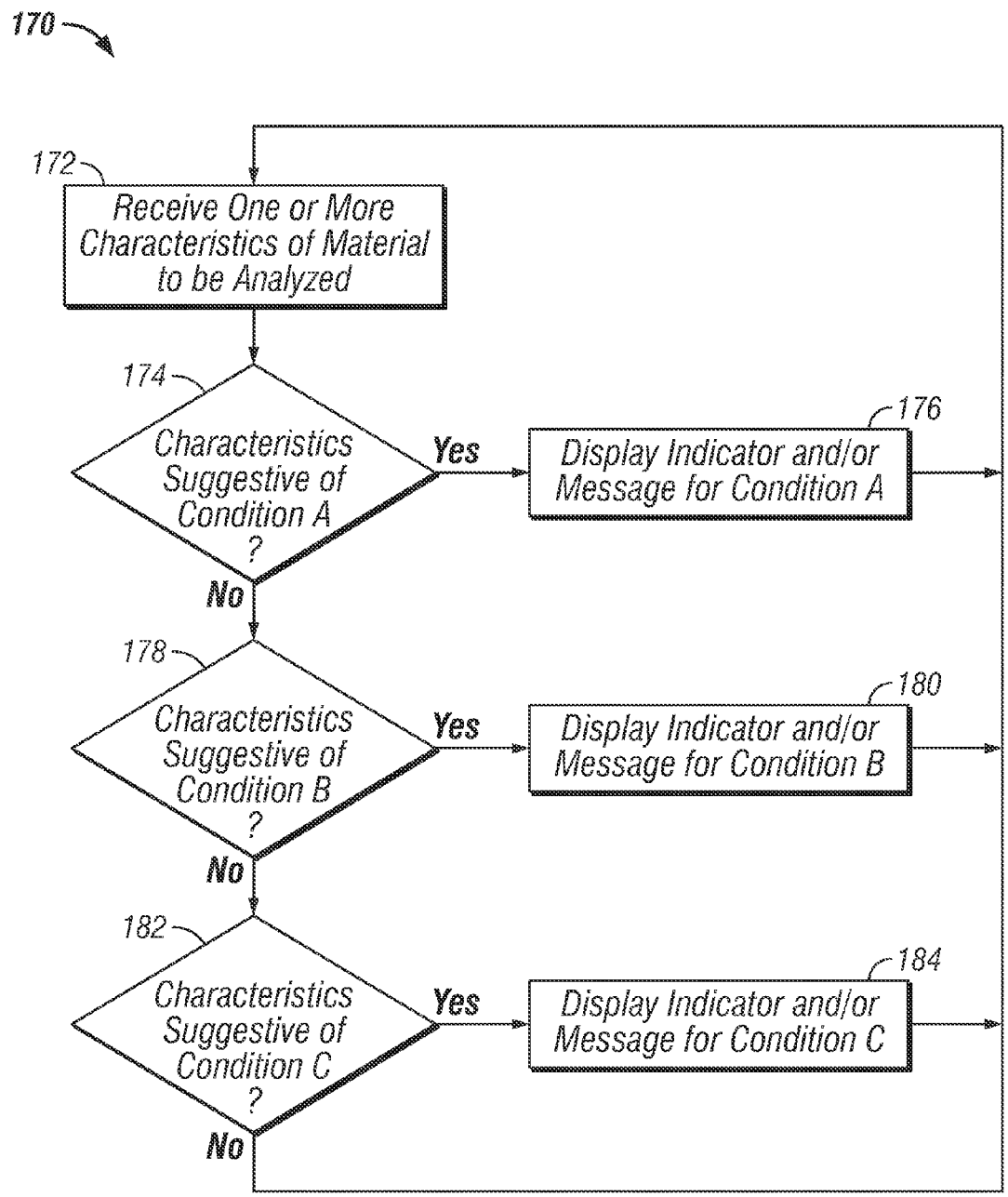
FIG. 12 is a flowchart of a method that may be used for the sensor to monitor and/or alert a user as to the status of the material to be analyzed.

FIG. 12 is a flowchart of a method that may be used for the sensor to monitor and/or alert a user as to the status of the material to be analyzed. FIG. 12 illustrates additional exemplary guidelines in the form of a flow chart 170. The flowchart 170 begins generally at block 172, where one or more characteristic(s) of the material to be analyzed are received. The one or more characteristic(s) is analyzed at block 174 to determine whether the characteristic(s) is suggestive of a first predefined condition (Condition A). Such a predefined condition may be, for example, low glucose or blood sugar level where the material to be analyzed is a biological material, and the determination may be performed using, for example, a lookup table of characteristics that can, but not necessarily, be specific to the particular user or individual using the sensor. If the determination at block 174 produces an affirmative answer, then an appropriate display indicator and/or message or other output to the user for the first predefined condition is provided at block 176. If the determination at block 174 produces a negative answer, then another determination is performed at block 178 to determine whether the characteristic(s) is suggestive of a second predefined condition (Condition B), which may be a normal glucose or blood sugar level condition. If yes, then an appropriate display indicator and/or message or other output for the second predefined condition is provided at block 180. If no, then a further determination is made at block 182 to determine whether the characteristic(s) is suggestive of a third predefined condition (Condition C), which may be a high glucose or blood sugar level condition. Once again, if the answer is affirmative, then an appropriate display indicator and/or message or other output for the third predefined condition is provided at block 184. Otherwise the flowchart 170 returns to block 172 to await receipt of additional characteristic(s) and/or other information to be analyzed.

Other and further embodiments utilizing one or more aspects of the inventions described above can be devised without departing from the spirit of Applicant's invention. For example, embodiments having the filter elements of FIGS. 2 and/or 8 could be combined with the embodiments having the switches in FIGS. 9 and/or 10. Various types, sizes, and amount of circuit components can be used to achieve a desired resonant response. Various types of EM energy, including electric fields created by applying discrete frequencies or pulses having wide band of frequencies, can be applied to the dispersive medium. Electrical permittivity, magnetic permeability, or a combination thereof can be used to determine the characteristics to be measured. Other variations are possible.

Further, the various methods and embodiments of the sensor system and methods herein can be included in combination with each other to produce variations of the disclosed methods and embodiments. Discussion of singular elements can include plural elements and vice-versa. References to at least one item followed by a reference to the item may include one or more items. Also, various aspects of the embodiments could be used in conjunction with each other to accomplish the understood goals of the disclosure. Unless the context requires otherwise, the word "comprise" or variations such as "comprises" or "comprising," should be understood to imply the inclusion of at least the stated element or step or group of elements or steps or equivalents thereof, and not the exclusion of a greater numerical quantity or any other element or step or group of elements or steps or equivalents thereof. The device or system may be used in a number of directions and orientations. The term "coupled, "coupling, "coupler," and like terms are used broadly herein and may include any method or device for securing, binding, bonding, fastening, attaching, joining, inserting therein, forming thereon or therein, communicating, or otherwise associating, for example, mechanically, magnetically, electrically, chemically, operably, directly or indirectly with intermediate elements, one or more pieces of members together and may further include without limitation integrally forming one functional member with another in a unitary fashion. The coupling may occur in any direction, including rotationally.

The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicant, but rather, in conformity with the patent laws, Applicant intends to protect fully all such modifications and improvements that come within the scope or range of equivalent of the following claims.

What is claimed is:

1. A sensor system for measuring responses to electromagnetic energy in a biological material to be analyzed, comprising:

a sensor comprising:
   a transmission line adapted to conduct an input signal of electromagnetic energy from a generator through an input port on the transmission line to an output port on the transmission line, the input signal composed of a series of ultra-wideband (UWB) pulses; and
   a plurality of resonant circuits having different resonant frequencies, conductively coupled to the transmission line between the input port and the output port and comprising one or more lumped circuit components to define the resonant frequencies for the resonant circuits, the one of the one or more lumped circuit components being adapted for coupling with a receiver, a controller and processor, and the biological material to be analyzed such that at least one circuit value of the resonant circuits is responsive to the biological material to be analyzed to determine a biological characteristic of the biological material, wherein the resonant circuits are adapted to cause the input signal on the transmission line to attenuate toward a different null value as the frequency content of the input signal approaches the resonant frequencies of the resonant circuits, each null value being located within a predefined frequency range that is different from predefined frequency ranges of other null values to produce an output signal through the output port.

2. The sensor system of claim 1, wherein at least one resonant circuit comprises a distributed element circuit component.

3. The sensor system of claim 1, wherein at least one resonant circuit comprises a combination of a lumped element circuit component and a distributed element circuit component.

4. The sensor system of claim 1, further comprising at least one switch coupled between at least one resonant circuit and the transmission line and adapted to control the operational state of the resonant circuit.

5. The sensor system of claim 4, further comprising one or more switches coupled between at least two circuit components of at least one of the resonant circuits and adapted to control the operational state of the circuit components relative to each other.

6. The sensor system of claim 5, wherein the one or more switches affect the resonant frequency of the at least one of the resonant circuits by switching the operational state of one or more circuit components on the at least one of the resonant circuits.

7. The sensor system of claim 4, further comprising at least one filter element coupled between the transmission line and at least one of the resonant circuits.

8. The sensor system of claim 1, further comprising the generator coupled to an input of the sensor, the receiver coupled to an output of the sensor, and the controller and processor coupled to the receiver.

9. The sensor system of claim 8, further comprising a switch coupled between the generator and the sensor and adapted to divide an input signal as a reference to the receiver.

10. The sensor system of claim 1, further comprising:
   the generator adapted to generate the input signal of electromagnetic energy;
   the receiver coupled to the sensor and adapted to receive a sensor output from the sensor; and
   the controller and processor coupled to the generator, the receiver, or a combination thereof and adapted to control a generation of the input signal from the generator, to process the sensor output from the receiver, or a combination thereof, the controller or processor configured to determine with the sensor output a biological characteristic of the biological material to be analyzed.

11. The sensor system of claim 10, wherein the input signal comprises a series of stepped frequencies.

12. A method of measuring one or more characteristics of a material responsive to electromagnetic energy, comprising:
   generating a signal of electromagnetic energy which spans an ultra-wideband range of frequencies;
   providing the signal as input to a sensor disposed at least in proximity to the material to affect the input signal as the input signal is transmitted through the material;
   transmitting the signal conductively along a transmission line of the sensor between an input port and an output port of the transmission line, the transmission line having a plurality of resonant circuits conductively coupled to the transmission line between the input port and the output port, the plurality of resonant circuits comprising one or more lumped circuit components to define resonant frequencies for the resonant circuits, wherein the resonant circuits having different resonant frequencies and at least one of the resonant circuits having a resonant frequency that is affected by the material;
   creating a short-circuit condition in the plurality of resonant circuits when a frequency content of the electromagnetic energy approaches at least one of the resonant frequencies of the plurality of resonant circuits;
   receiving an output signal from the sensor, the output signal representative of the input signal being subjected to the short-circuit condition during transmission through the sensor at frequencies approaching the at least one of the resonant frequencies of the plurality of resonant circuits; and
   processing the output signal with the short-circuit condition related to the at least one of the resonant frequencies to determine the one or more characteristics of the material.

13. The method of claim 12, wherein processing the output signal comprises preparing a time domain representation of the electromagnetic energy from the output signal.

14. The method of claim 12, wherein processing the output signal comprises preparing a frequency domain representation of the electromagnetic energy from the output signal.

15. The method of claim 14, further comprising identifying portions of the input signal exhibiting the short-circuit condition and comparing the frequency domain representation or portions thereof to a known frequency domain representation to identify the one or more characteristics of the material.

16. The method of claim 12, wherein generating a signal of electromagnetic energy comprises generating a pulse, the pulse having a frequency composition that spans the ultra-wideband range of frequencies.

17. The method of claim 12, wherein generating a signal of electromagnetic energy comprises generating a series of stepped frequencies.

18. The method of claim 12, further comprising filtering a response from the resonant circuits to the transmission line for at least some reflections of the input signal.

19. The method of claim 12, further comprising switching an operational state of the plurality of resonant circuits to control operation of the plurality of resonant circuits with the transmission line.

20. The method of claim 12, further comprising switching an operational state of at least one circuit component of the resonant circuits to change at least one of the resonant frequencies of the resonant circuits.

21. The method of claim 20, further comprising measuring different resonant frequencies with the resonant circuits by switching the operational state of the at least one circuit component of the resonant circuits.

22. The method of claim 21, further comprising processing at least one output signal from the sensor to establish a signature that correlates to one or more known characteristics of a first material.

23. The method of claim 22, wherein processing the output signal to determine the one or more characteristics of the material further comprises processing one or more other output signals from the first material under conditions having one or more unknown characteristics or a different material than the first material having one or more unknown characteristics, and correlating results for the one or more unknown characteristics to the signature for the one or more known characteristics.

24. The method of claim 22, wherein the signature comprises a permittivity or permeability curve at various frequencies.

\* \* \* \* \*